(12) United States Patent  
Giudiceandrea

(10) Patent No.: US 8,250,922 B2
(45) Date of Patent: Aug. 28, 2012

(54) METHOD AND APPARATUS FOR IDENTIFYING THE MODULUS OF ELASTICITY OF LOGS

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 463 days.

(21) Appl. No.: 12/552,827

(22) Filed: Sep. 2, 2009

(65) Prior Publication Data

US 2010/0064810 A1    Mar. 18, 2010

(30) Foreign Application Priority Data

Sep. 18, 2008  (IT) .............................. VR2008A0105

(51) Int. Cl.
*G01N 29/02*      (2006.01)
*B07C 5/14*       (2006.01)

(52) U.S. Cl. .............................. 73/597; 73/602; 209/517

(58) Field of Classification Search ............... 73/579, 73/597, 602, 78, 587, 594; 702/56; 209/517–518, 209/596–598
See application file for complete search history.

(56) References Cited

U.S. PATENT DOCUMENTS

| | | | |
|---|---|---|---|
| 4,930,386 A * | 6/1990 | Laskowski et al. ............. | 83/399 |
| 6,026,689 A * | 2/2000 | Snyder et al. .................... | 73/602 |
| 6,782,732 B2 * | 8/2004 | Huang et al. .................. | 73/12.07 |
| 7,383,730 B2 * | 6/2008 | Huang et al. .................... | 73/597 |
| 7,603,904 B2 * | 10/2009 | Harris et al. .................... | 73/597 |
| 2008/0197054 A1 * | 8/2008 | Lindstrom ..................... | 209/517 |
| 2008/0295602 A1 * | 12/2008 | Wallace .......................... | 73/602 |
| 2011/0030481 A1 * | 2/2011 | Giudiceandrea ............... | 73/831 |

FOREIGN PATENT DOCUMENTS

WO         9944059 A1    9/1999

* cited by examiner

*Primary Examiner* — Helen C. Kwok

(74) *Attorney, Agent, or Firm* — Pearne & Gordon LLP

(57) ABSTRACT

An apparatus for identifying the modulus of elasticity of logs includes a device (2) equipped for detecting at least one log (T) eigenfrequency (natural frequency) and with a plurality of supports (10) able to move by rotating between a pick up position, in which they are located at a loading station (7), and a release position in which they are located at an unloading station (8) which is on the opposite side of a supports (10) axis of rotation relative to the loading station (7). A method for identifying the modulus of elasticity of logs includes the steps of picking up a log (T) while it is fed along a first direction (A1) on a first conveyor line (102); subjecting the log (T) to a step of detecting at least one natural frequency; and a step of releasing the log (T) on a second conveyor line (103) defining a second feed direction (A2) which is transversal to the first conveying direction (A1).

22 Claims, 3 Drawing Sheets

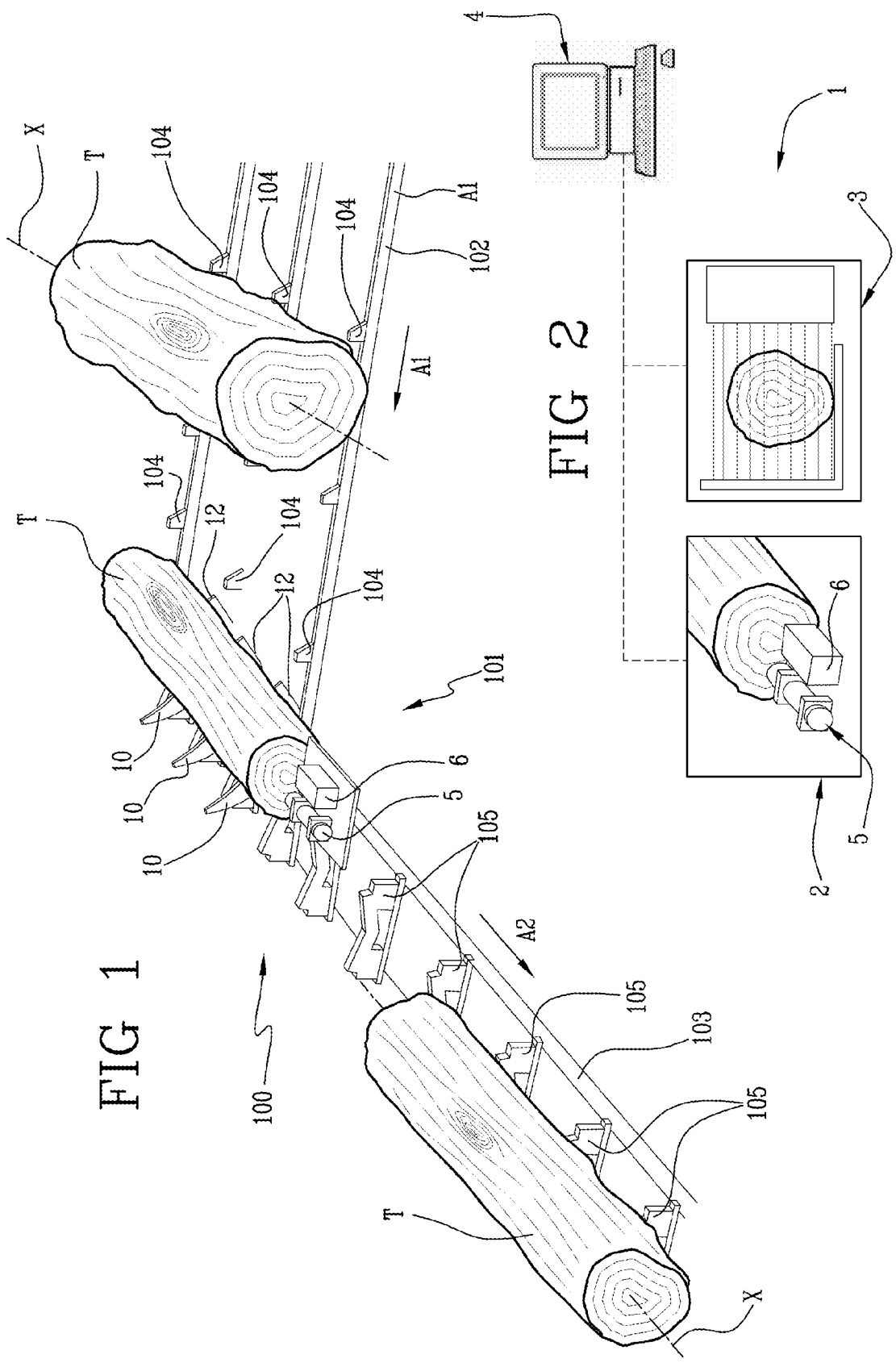

METHOD AND APPARATUS FOR IDENTIFYING THE MODULUS OF ELASTICITY OF LOGS

FIELD OF THE INVENTION

The present invention relates to a method for identifying the modulus of elasticity of logs. The present invention also relates to an apparatus for identifying the modulus of elasticity of logs, in particular of the type which can be implemented in systems for storing and processing logs.

DESCRIPTION OF RELATED ART

It is known that, in systems for storing and processing logs such as sawmills, the logs are graded individually to store physical/mechanical data about them such as the mass, geometry, modulus of elasticity and distribution of knots. With reference to identifying the modulus of elasticity, there are suitable detection stations which measure the density of the wood forming the log and also identify the main eigenfrequencies (natural frequencies) of the log. Knowledge of the natural frequencies and the density of the wood allows subsequent calculation of the modulus of elasticity of the log detected.

In prior art systems there are respectively a station for detecting the density of the wood and a station for detecting the natural frequencies. Said stations are positioned along a log feed line which usually comprises a continuous conveyor.

The station for detecting the natural frequencies of the log comprises a device which generates an impact on one of the two faces of the log, normally using a suitably sized hammer, then detects an acoustic emission caused by the impact, or alternatively optically detects a consequent log vibration. The data detected is then processed to obtain the main natural frequencies of the log. To do that, the log is picked up from the feed line, then subjected to the detection treatment and then put back on the feed line substantially in the same position from where it was picked up.

Disadvantageously, said detection station has significant dimensions and is complex basically due to the need to house suitable lifting equipment which has significant dimensions, being designed to lift and transfer logs with a considerable mass.

Moreover, log transfer from the feed line to the detection station and the subsequent return to the feed line result in down times which may be significant and consequently increase the times for which the log remains in the system. Obviously, this has a negative impact on system productivity.

BRIEF SUMMARY OF THE INVENTION

In this context, the technical purpose of the present invention is to provide an apparatus and a method for identifying the modulus of elasticity of logs which overcomes the above-mentioned disadvantages.

In particular, the present invention has for an aim to provide an apparatus and a method for identifying the modulus of elasticity of logs which allows system overall dimensions to be reduced.

The present invention also has for an aim to provide an apparatus and a method for identifying the modulus of elasticity of logs which reduces the complexity of the system.

The present invention also has for an aim to provide an apparatus and a method for identifying the modulus of elasticity of logs which allows system productivity to be increased.

The technical purpose indicated and the aims specified are substantially achieved by an apparatus and a method for identifying the modulus of elasticity of logs comprising the technical features set forth herein.

The invention also relates to a system for processing logs which has the features set forth herein.

BRIEF DESCRIPTION OF THE SEVERAL VIEWS OD THE DRAWING

Further features and advantages of the present invention are more apparent from the non-limiting description which follows of a preferred, non-limiting embodiment of an apparatus and a method for identifying the modulus of elasticity of logs, illustrated in the accompanying drawings, in which:

FIG. 1 is a perspective view of a portion of a system for processing logs using an apparatus for identifying the modulus of elasticity of logs according to the present invention;

FIG. 2 is a schematic view of an apparatus for detecting the modulus of elasticity of logs according to the present invention;

DETAILED DESCRIPTION OF THE INVENTION

Figure 3A:
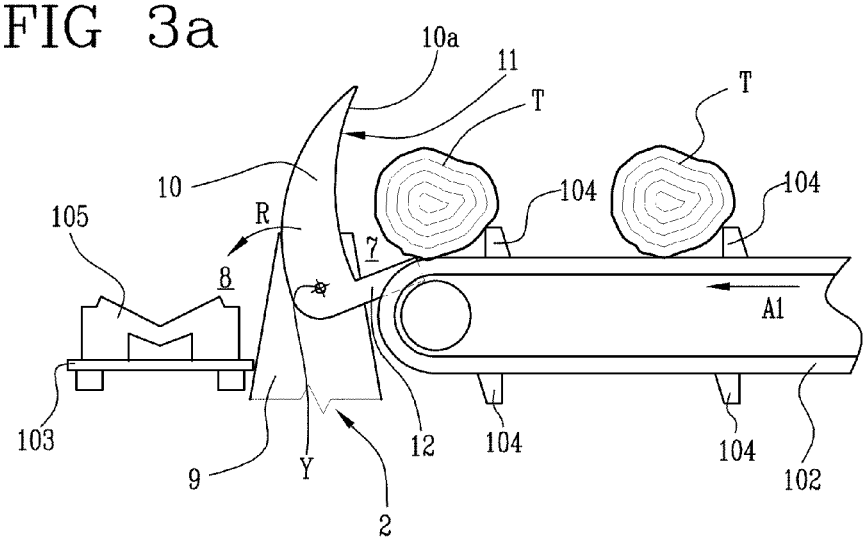
FIGS. 3a to 3c are three front views of a part of the apparatus according to the present invention and according to three different operating steps.

An apparatus for identifying the modulus of elasticity of logs, and in particular of logs of cut timber, according to the present invention is schematically illustrated and labelled 1 as a whole in FIG. 2. The apparatus 1 comprises a device 2 for detecting at least one natural frequency of a log and equipment 3 for measuring the density of the log. The device 2 is described in detail below, whilst the equipment 3, of the known type usually including an X-ray measurer or alternatively scales for measuring the mass of the log "T" (to obtain the density), is not described in further detail. The apparatus 1 also comprises a processing unit 4 which receives from the device 2 and the equipment 3 the natural frequencies and density values relating to a log and processes them to identify a log modulus of elasticity value. The processing of the natural frequency and density values, to identify the modulus of elasticity, is carried out according to known procedures which are not described in detail here.

According to the present invention, the device 2 for detecting at least one natural frequency can be used in a system for processing wood, part of which is shown in FIG. 1 and labelled 100. Advantageously, for reasons which will be explained below, the device 2 is positioned at a transfer station 101 located between a first conveyor line 102 and a second conveyor line 103, whilst the equipment 3 may be located at any point of the system 100.

The conveyor lines 102, 103 are of the continuous belt or chain type and move the logs, labelled "T", along respective feed lines inside the system 100. At the transfer station 101, the first and second conveyor lines 102, 103 define respective feed directions "A1", "A2" which are transversal to each other, preferably perpendicular.

In more detail, on the first conveyor line 102 the logs "T" are fed perpendicularly to a longitudinal axis "X" of the logs "T", whilst on the second conveyor line 103 the logs "T" are fed parallel with a longitudinal axis "X" of the logs "T".

The first conveyor line 102 has a plurality of pusher blocks 104, spaced out at equal distances from each other in parallel rows so that each log "T" is pulled forwards by more than one pusher block 104 simultaneously. In contrast, the second conveyor line 103 comprises a succession of supporting brackets 105 forming respective concave holders for stably supporting part of a log "T", so that the log "T" can be supported by two or more supporting brackets 105 simultaneously.

The device 2 for detecting at least one natural frequency of a log "T" is at the transfer station 101. The device is designed to transfer the log "T" from the first conveyor line 102 to the second conveyor line 103, and simultaneously to subject the log "T" to a measurement of at least one of its natural frequencies. In detail, as shown in FIG. 1, the device 2 comprises a hammer 5, or any other element designed to generate a mechanical impact on a portion of the log "T", and a detector 6 which detects a log "T" vibration using optical systems (for example laser) or acoustic systems (for example a microphone). The vibration detected is then sent to the processing unit 4. The hammer 5 and the detector 6 therefore form detection means acting on the log "T", and in particular on a front face of the log "T", for imparting a mechanical perturbation to the log "T" and detecting a consequent log vibration or acoustic emission. More generally, the detection means 5, 6 cause a mechanical perturbation in the log "T" by a percussion (impact force) effect on the log "T".

Figure 3B:
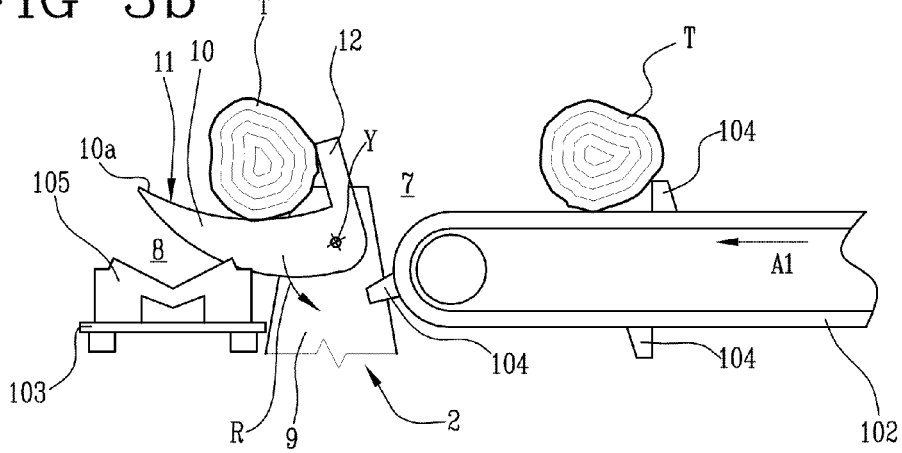
Figure 3C:
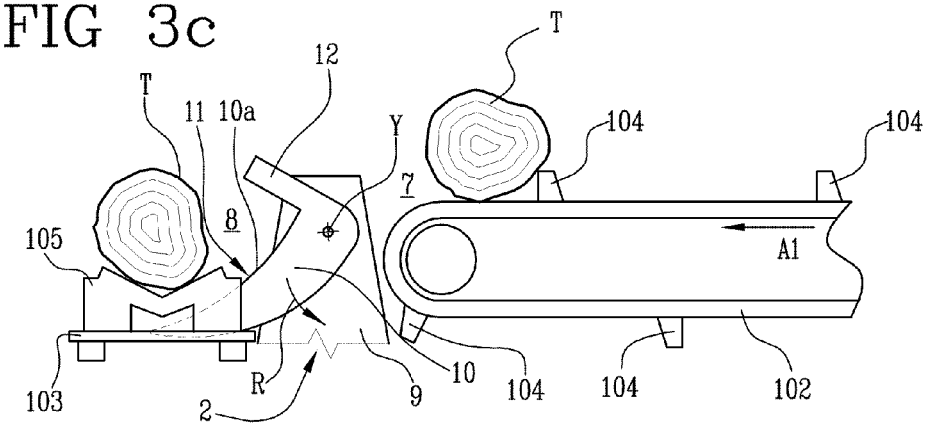

FIG. 1, and even more clearly FIGS. 3a-3c, show the structure of the device 2 for detecting at least one log "T" natural frequency.

The device 2 has a loading station 7, facing towards the first conveyor line 102 and communicating with it to receive a log "T" to be detected, and an unloading station 8, communicating with the second conveyor line 103 for releasing a log "T" onto it.

The device 2 comprises a frame 9 on which at least one support 10 is mounted, able to rotate about a fixed hinge axis "Y". The support can rotate between a pick up position, illustrated in FIG. 3a, and a release position, illustrated in FIG. 3c. In the pick up position the support 10 is located at the loading station 7 to receive a log "T", whilst in the release position the support 10 is located at the unloading station 8 to release a log "T" onto the second conveyor line 103. The hinge axis "Y" is positioned perpendicularly to the feed direction "A1" of the first conveyor line 102. Moreover, the loading station 7 and the unloading station 8 are positioned on opposite sides of the hinge axis "X".

In the preferred embodiment, the device 2 comprises three supports 10 able to rotate about the same hinge axis "Y" and positioned, along the hinge axis "Y", inserted between the pusher blocks 104 of the first conveyor line 102 so that during rotation about the hinge axis "Y" the supports 10 do not interfere with the pusher blocks 104. The three supports 10, integral with each other, each have a thin shape substantially forming a supporting blade for a log "T". According to alternative embodiments, not illustrated, the device 2 may comprise two or four or more supports 10, aligned along the hinge axis "Y" and integral with each other.

The device 2 also comprises motor means, not illustrated, for example an electric motor, connected to the supports 10 for moving the supports between the pick up and release positions.

Each support 10 has a supporting surface 10a intended to make contact with a lower portion of the log "T" and, after support 10 rotation, to move the log "T" away from the first conveyor line 102. The supporting surface 10a has a curved portion, and in particular a hollow 11 facing upwards when the support 10 is at the loading station 7.

Each support 10 is designed to retain a log "T" during a rotation about the hinge axis "Y" and to release the log "T" due to the effect of gravity onto the second conveyor line 103 at the end of the rotation. In more detail, each support 10 has a projection 12 extending away from the hollow 11 and, in conjunction with the hollow 11, giving the support 10 what is preferably an "L" shape, suitable for picking up the log "T" while it is initially supported by the first conveyor line 102. In particular, the projection 12 forms a lateral support for the log "T" which rests on the hollow 11.

During rotation of the supports 10 from the pick up position (FIG. 3a) towards the release position (FIG. 3c), there is an intermediate operating position illustrated in FIG. 3b where the log "T", supported by the supports 10, is opposite the detection means 5, 6 so that it can be subjected to the detection of at least one natural frequency. In particular, a substantially flat front surface of the log "T" is positioned opposite the detection means 5, 6 whilst the supports 10 and the log "T" are kept in a fixed position until the end of the detection step. At the end of the detection step, the supports 10 continue their rotating motion towards the unloading station 8 until they reach the release position.

Figure 4:
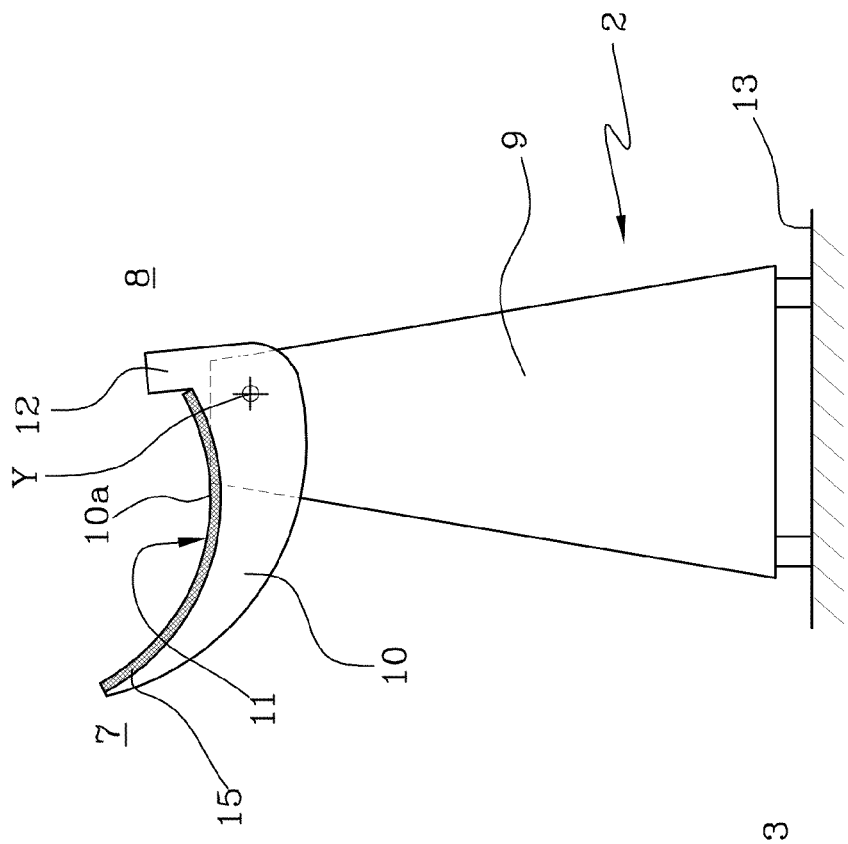
FIG. 4 is a front view of a first embodiment of a portion of the apparatus according to the invention.
Figure 5:
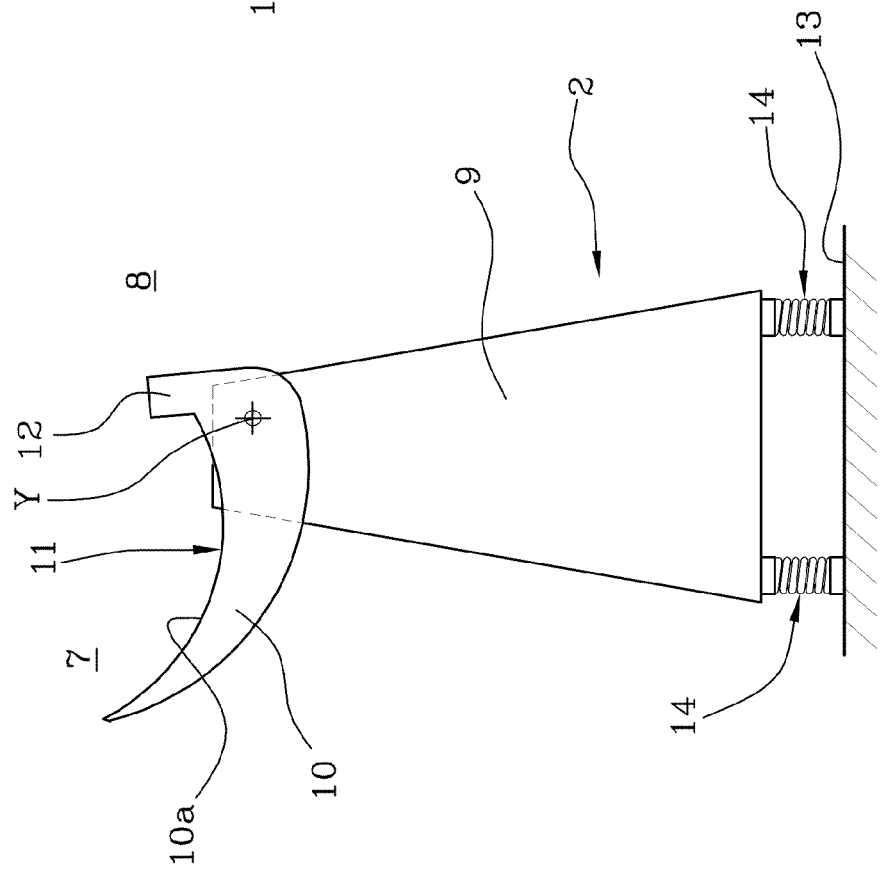
FIG. 5 is a front view of a second embodiment of the portion of apparatus illustrated in FIG. 3.

FIGS. 4 and 5 show two different embodiments of the device 2 for detecting at least one log "T" natural frequency, and in particular show the connection between the frame 9 and a frame 9 support surface 13. According to the first embodiment, shown in FIG. 4, the frame 9 is connected to the respective support surface 13, that is to say, to the ground, by elastic means 14 designed to reduce the transmission of vibrations between the frame 9 and the ground. Use of the elastic means 14 is particularly important, since the vibration to which the log "T" is subjected following operation of the detection means 5, 6 is greatly influenced by the ways in which the frame 9 and the supports 10 on which the log "T" rests directly vibrate. The vibrating connection between the log "T" and the assembly consisting of the frame 9 and the supports 10 means that the frequency response detected by the detector 6 is distorted by the vibrations transmitted between the log "T" and the frame 9 and the supports 10 and is therefore different to the frequency response which would be obtained from the log "T" alone. In this case, by identifying in advance the inertial properties of the device 2 and suitably sizing the frame 9 and the elastic means 14, it is possible to detect the frequency response of the log "T" supported by the supports 10 and to obtain, by means of suitable numerical calculation, the desired log "T" natural frequency values.

In the embodiment illustrated in FIG. 4, the elastic means 14 comprise a plurality of helical springs. According to an embodiment not illustrated, the elastic means 14 comprise rubber blocks or other elastically deformable supports.

FIG. 5 shows a different embodiment in which there is a suspension stage directly between the log "T" and the supports 10. In more detail, each support 10 is at least partly coated with a layer of elastic material 15 at a portion of the support 10 intended to make contact with the log "T". The layer of elastic material 15, preferably made of rubber, a least partly covers the hollow 11 of the support 10 and is suitably sized to reduce a dynamic connection between the log "T" and the supports 10. Therefore, the presence of the layer of elastic material 15 substantially has the effect of uncoupling the log "T" frequency response from the device 2 frequency response, so that the frequency response detected by the detector 6 already has the effects of distortion from other structural elements of the device 2 removed. Therefore, in this latter embodiment, the elastic means 14 interposed between the frame 9 and the ground may be omitted.

An embodiment not illustrated includes both the layer of elastic material 15 coating the supports 10 and elastic means 14 between the frame 9 and the ground.

According to another alternative embodiment not illustrated, the supports 10 are connected to scales to identify the mass of the logs "T" while they are supported by the supports 10 and in particular the device 2 supports 10 coincide with scales supports. Knowledge of the mass of the log "T" allows, after identification of the volume of the log "T", the average density to be obtained. In that case, the equipment 3 for measuring the density of the log "T" substantially coincides with the device 2 for detecting at least one log "T" natural frequency.

Device 2 operation is described below.

A log "T", conveyed by the first conveyor line 102, reaches the device 2 loading station 7. In particular, the log "T" reaches the loading station 7 while being fed along a direction "A1" which is transversal, preferably perpendicular, to the longitudinal axis "X" of the log "T".

At the loading station, the device 2 projections 12 are in a position in which they are inserted between the pusher blocks 104 of the first conveyor line 102 and do not interfere with the pusher blocks 104 so that the log "T" can move over the supports 10. As soon as the log "T" is on top of the supports 10, the first conveyor line 102 releases it onto the support 10 supporting surfaces 10a which support it for a subsequent step of detecting at least one natural frequency. Preferably, once the they received the log "T", the supports 10 rotate about the hinge axis "Y" and in particular they are lowered to move the log "T" away from the first conveyor line 102. Said rotation is then interrupted to retain the log "T" in the operating position in which a portion of the log "T" is opposite the detection means 5, 6. The detection means 5, 6 may then apply a mechanical percussion action to said portion of the log "T", and in particular on a front face, then detect (optically or acoustically) a consequent log "T" vibration.

After the detection step, the supports 10 are again rotated about the hinge axis "Y", in particular in the same direction of rotation as previously, releasing the log "T" due to the effect of gravity onto the supporting brackets 105 of the second conveyor line 103, which near to the device 2 defines a feed direction "A2" which is substantially parallel with the longitudinal axis "X" of the log "T" and, therefore, transversal to the conveying direction "A1" of the first conveyor line 102. During the log "T" release step, the supports 10 are in a position in which they are inserted between the supporting brackets 105 of the second conveyor line 103.

During the steps of picking up the log "T" from the first conveyor line 102 and releasing the log "T" on the second conveyor line 103, and preferably during all steps for moving the log "T" across the device 2, the log "T" is moved along directions which are transversal, preferably perpendicular, to the longitudinal axis "X" of the log "T".

Moreover, during the steps of picking up the log "T" from the first conveyor line 102 and releasing the log "T" on the second conveyor line 103, and preferably during all steps for moving the log "T" across the device 2, the log "T" is substantially kept orientated along the same direction.

The present invention achieves the preset aims, overcoming the disadvantages of the prior art.

Installing the device for detecting at least one natural frequency at the transfer station means that the feed movement of the conveyor lines does not have to be interrupted and allows the steps of detecting and transferring logs to be combined, allowing them to be carried out simultaneously with obvious advantages in terms of the time taken.

Moreover, combining the detection means with supports of the type described allows a considerable simplification in terms of construction, providing a simple, sturdy structure. At the same time, by including the transfer and detection steps in a single transfer station, overall system dimensions are reduced.

The invention claimed is:

1. An apparatus for identifying a modulus of elasticity of logs, comprising a device (2) for detecting at least one eigenfrequency of a log (T), the device (2) having a log (T) loading station (7) and a log (T) unloading station (8) and comprising:
   at least one support (10) which can move between a pick up position, in which the support (10) is placed at the loading station (7), and a release position, in which the support (10) is placed at the unloading station (8), the support (10) having at least one supporting surface (10a) designed to support a bottom of the log (T);
   means (5, 6) for detecting at least one eigenfrequency of the log (T);
   the apparatus being characterised in that the support (10) can rotate about a hinge axis (Y) at least between the pick up position and the release position to transfer the log (T) from the loading station (7) to the unloading station (8), the loading station (7) and the unloading station (8) being positioned on opposite sides of the hinge axis (Y), said detection means (5, 6) acting on the log (T) while the log (T) is supported on the support (10).

2. The apparatus according to claim 1, characterised in that the detection means (5, 6) use a percussion action to induce a mechanical perturbation in the log (T).

3. The apparatus according to claim 1, characterised in that the hinge axis (Y) is fixed.

4. The apparatus according to claim 1, characterised in that the supporting surface (10a) has a hollow (11) designed to stably retain by the log (T) on the support (10) by means of gravity.

5. The apparatus according to claim 1, characterised in that the support (10) can also rotate about the hinge axis (Y) to adopt an operating position in which the support (10) stably supports the log (T), allowing the detection means (5, 6) to operate on the log (T).

6. The apparatus according to claim 5, characterised in that the support (10) operating position defines a support (10) rotated intermediate position which is between the pick up position and the release position.

7. The apparatus according to claim 1, characterised in that the device (2) for detecting at least one eigenfrequency comprises a frame (9) on which the support (10) is rotatably mounted, the device (2) comprising one or more elements (14) having an elastic function, inserted between the frame (9) and a support surface (13) on which the frame rests (9) so as to increase a dynamic insulation between the frame (9) and the support surface (13) on which the frame (9) rests.

8. The apparatus according to claim 1, characterised in that the supporting surface (10a) is at least partly coated with an elastic material to increase a dynamic insulation between the support (10) and the log (T) supported by the support (10).

9. The apparatus according to claim 1, characterised in that the device (2) for detecting at least one eigenfrequency comprises a plurality of supports (10) which are aligned along the hinge axis (Y) and which are spaced so that the supports (10) are inserted between corresponding log (T) pusher blocks (104), said pusher blocks (104) being part of a first log (T) conveyor line (102).

10. The apparatus according to claim 1, characterised in that the device (2) comprises motor means connected to the support (10) for moving between the pick up and release positions.

11. The apparatus according to claim 1, characterised in that the device (2) transfers the log (T) between the loading station (7) and the unloading station (8) substantially keeping the log orientated along the same direction.

12. The apparatus according to claim 1, characterised in that the device (2) transfers the log (T) between the loading station (7) and the unloading station (8), moving the log (T) transversally to a longitudinal axis (X) of the log (T).

13. A method for identifying a modulus of elasticity of logs, comprising the steps of:
  picking up a log (T) as the log (T) is fed along a first direction (A1) on a first conveyor line (102);
  subjecting the log (T) to a step of detecting at least one eigenfrequency;
  the method being characterised in that the method comprises, after the detection step, a step of releasing the log (T) onto a second conveyor line (103) defining a second direction of feed (A2) which is transversal to the first direction (A1).

14. The method according to claim 13, characterised in that the log (T) pick up step, the detection step and the log (T) release step are carried out while keeping the log (T) substantially orientated along the same direction.

15. The method according to claim 13, characterised in that the log (T) pick up step and the log (T) release step are carried out by moving the log (T) transversally to a longitudinal axis (X) of the log (T).

16. The method according to claim 13, characterised in that the log (T) pick up step comprises a first step of rotating at least one support (10) about a fixed hinge axis (Y), allowing the support (10) to intercept a lower portion of the log (T) thus disengaging the log (T) from the first conveyor line (102).

17. The method according to claim 16, characterised in that the step of subjecting the log (T) to the detection step takes place by interrupting the rotation of the support (10) in a predetermined position at which a portion of the log (T) is placed opposite a means (5, 6) for detecting at least one log (T) eigenfrequency.

18. The method according to claim 17, characterised in that the log (T) release step takes place after the detection step and is carried out by a second step of rotating the support (10) about the hinge axis (Y) until the log (T) is released by the effect of gravity onto the second conveyor line (103), the first and second steps of rotating the support (10) about the hinge axis (Y) being performed according to the same direction of rotation.

19. The method according to claim 13, characterised in that the step of subjecting the log (T) to a step for detecting at least one eigenfrequency comprises a step of subjecting the log (T) to a mechanical percussion action and a subsequent step of detecting a consequent log (T) vibration.

20. A system for processing logs, comprising:
  a first conveyor line (102) for logs (T);
  a second conveyor line (103) for logs (T);
  a transfer station (101) inserted between the first and second conveyor lines (102, 103) for transferring the logs (T) from the first conveyor line (102) to the second conveyor line (103); the conveyor lines (102, 103), at the transfer station (101), defining respective directions of feed (A1, A2) which are transversal to each other;
  an apparatus for identifying a modulus of elasticity of a log (T), the apparatus comprising a device (2) for detecting at least one eigenfrequency of the log (T), the device (2) having a log (T) loading station (7) and a log (T) unloading station (8);
  the system (100) being characterised in that the device (2) for detecting at least one eigenfrequency is positioned at the transfer station (101), in such a way that the loading station (7) is fed by the first conveyor line (102) and the unloading station (8) is facing towards the second conveyor line (103).

21. The system according to claim 20, characterised in that the device (2) comprises at least one movable support (10) for transferring the log (T) from the loading station (7) towards the unloading station (8), the support (10) also moving to adopt an operating position in which the support (10) stably supports the log (T) and keeps the log (T) opposite a means (5, 6) for detecting at least one log (T) eigenfrequency.

22. A system for processing logs, comprising:
  a first conveyor line (102) for logs (T);
  a second conveyor line (103) for logs (T);
  a transfer station (101) inserted between the first and second conveyor lines (102, 103) for transferring the logs (T) from the first conveyor line (102) to the second conveyor line (103); the conveyor lines (102, 103), at the transfer station (101), defining respective directions of feed (A1, A2) which are transversal to each other;
  an apparatus for identifying a modulus of elasticity of a log (T), the apparatus comprising a device (2) for detecting at least one eigenfrequency of the log (T), the device (2) having a log (T) loading station (7) and a log (T) unloading station (8);
  the system (100) being characterised in that the device (2) for detecting at least one eigenfrequency is positioned at the transfer station (101), in such a way that the loading station (7) is fed by the first conveyor line (102) and the unloading station (8) is facing towards the second conveyor line (103), and that the apparatus for identifying the modulus of elasticity of a log (T) is an apparatus according to claim 1.

* * * * *